United States Patent [19]

Ebling et al.

[11] Patent Number: 5,347,990
[45] Date of Patent: Sep. 20, 1994

[54] ENDOSCOPE WITH STERILE SLEEVE

[75] Inventors: Wendell V. Ebling, 21131 Kensington La., Lake Forest, Calif. 92630; J. Charles Elmore, Mission Viejo, Calif.

[73] Assignee: Wendell V. Ebling, Lake Forest, Calif.

[21] Appl. No.: 959,272

[22] Filed: Oct. 8, 1992

[51] Int. Cl.5 ................................................ A61B 1/00
[52] U.S. Cl. ................................................ 128/4; 128/6
[58] Field of Search ......................................... 128/4, 6

[56] References Cited

U.S. PATENT DOCUMENTS

| | | | |
|---|---|---|---|
| 2,922,415 | 1/1960 | Campagna | 128/4 |
| 3,144,020 | 8/1964 | Zingale | 128/4 |
| 3,162,190 | 12/1964 | Del Gizzo | 128/6 |
| 3,794,091 | 2/1974 | Ersek et al. | 150/52 R |
| 3,809,072 | 5/1974 | Ersek et al. | 128/23 |
| 3,866,601 | 2/1975 | Russell | 128/4 |
| 3,947,089 | 3/1976 | Rapp | 350/151 |
| 3,980,078 | 9/1976 | Tominaga | 128/4 |
| 4,076,018 | 2/1978 | Heckele | 128/6 |
| 4,085,742 | 4/1978 | Okada | 128/4 |
| 4,132,227 | 1/1979 | Ibe | 128/4 |
| 4,201,199 | 5/1980 | Smith | 128/7 |
| 4,248,214 | 2/1981 | Hannah | 128/7 |
| 4,254,762 | 3/1981 | Yoon | 128/4 |
| 4,327,735 | 5/1982 | Hampson | 128/348 |
| 4,329,995 | 5/1982 | Anthracite | 128/350 R |
| 4,624,243 | 11/1986 | Lowery et al. | 128/6 |
| 4,646,722 | 3/1987 | Silverstein | 128/4 |
| 4,647,149 | 3/1987 | McCartney et al. | 350/96.20 |
| 4,757,381 | 7/1988 | Cooper et al. | 358/98 |
| 4,770,653 | 9/1988 | Shturman | 604/21 |
| 4,776,340 | 10/1988 | Moran et al. | 128/634 |
| 4,869,238 | 9/1989 | Opie et al. | 128/6 |
| 4,916,534 | 4/1990 | Takahashi et al. | 128/6 X |

FOREIGN PATENT DOCUMENTS 1405025  9/1975  United Kingdom .

OTHER PUBLICATIONS

Designer's Handbook: Medical Electronics, "Hybrid Cables Reduce Clutter and Failures", pp. 10–11.
Fiber Optics Handbok For Engineers and Scientists, Chapter 2, "Fiber-Optic Cables", by M. M. Ramsay, 12 pages.
Collimated Holes, Inc., "Flexible Fiber Bundles and Light Guide Materials Pages".

Primary Examiner—Richard J. Apley
Assistant Examiner—Beverly A. Meindl
Attorney, Agent, or Firm—Stetina and Brunda

[57]  ABSTRACT

An endoscope has a fiber optic image bundle which is insertible into a separate sterile sleeve such that the fiber optic image bundle need not be sterilized prior to use. A window formed proximate the distal end of the sleeve facilitates viewing through the fiber optic image bundle. A biasing means urges the fiber optic image bundle into abutment with the window to facilitate proper optical alignment thereof.

28 Claims, 2 Drawing Sheets

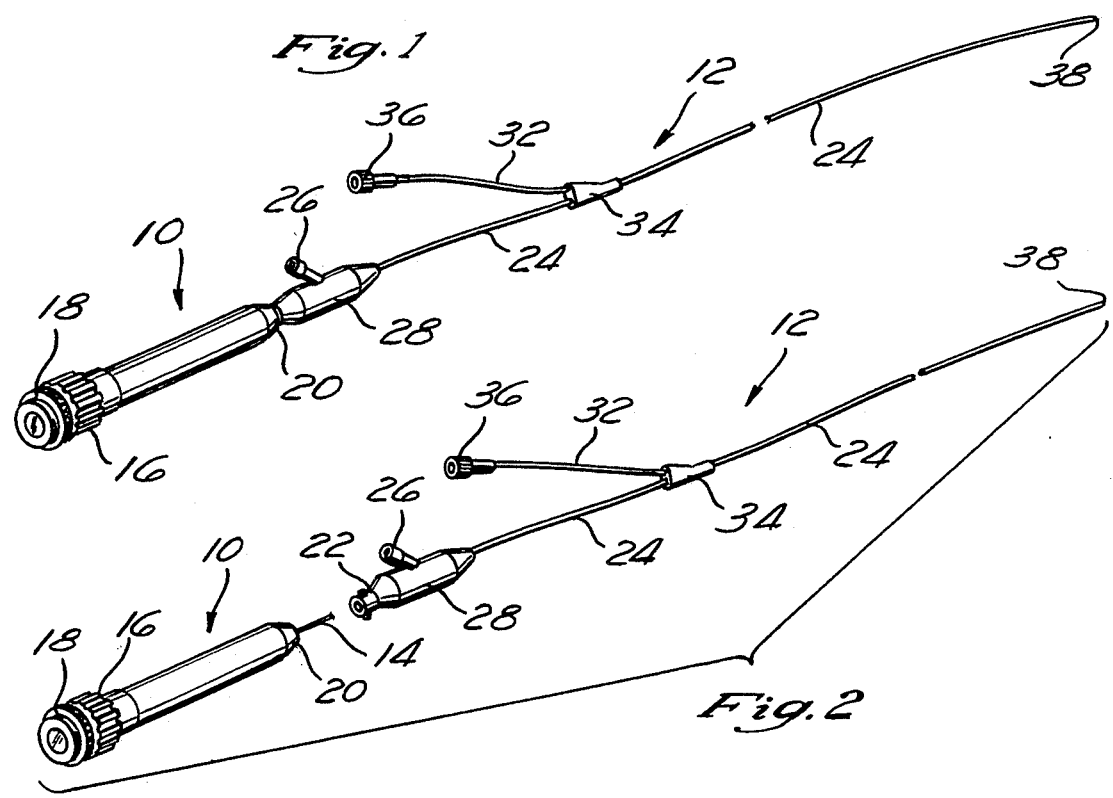
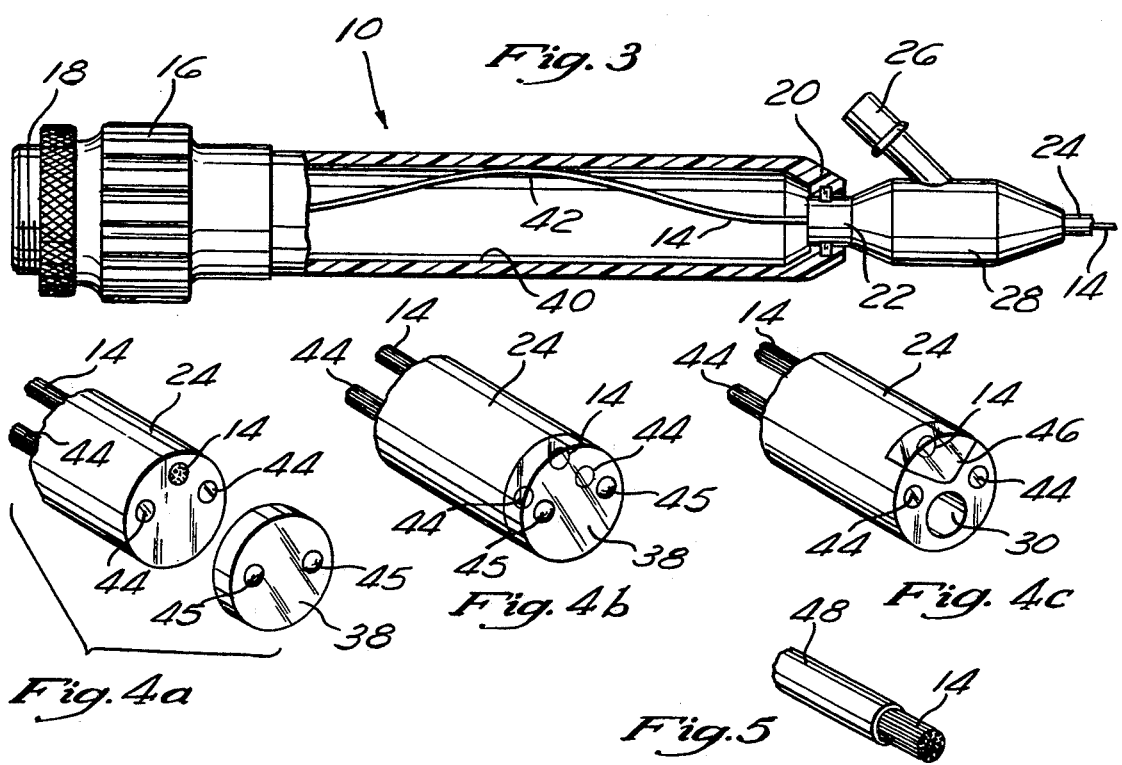

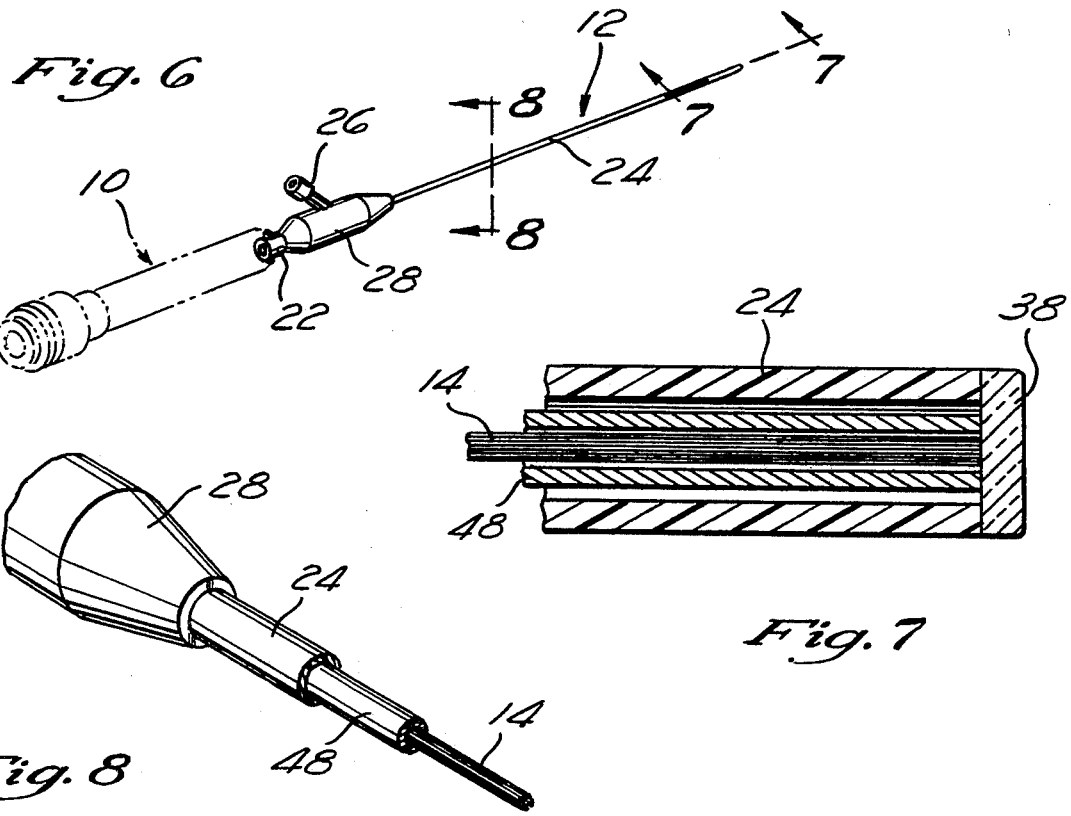
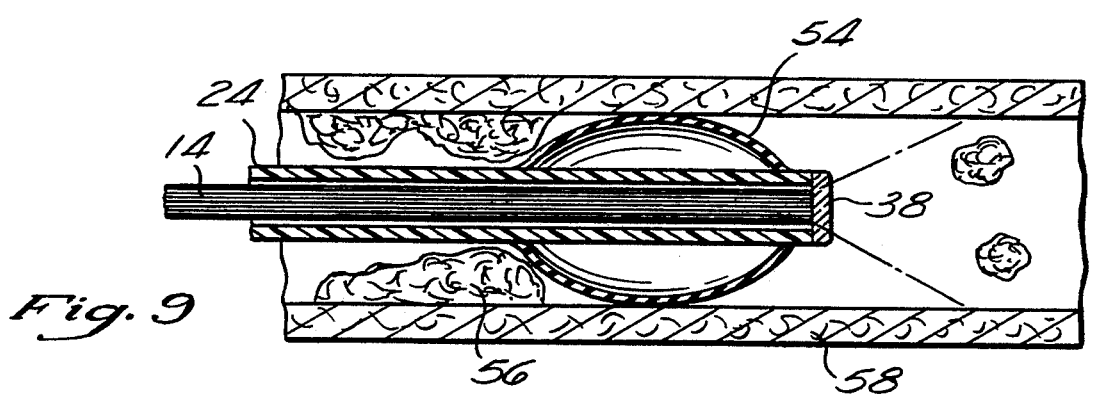
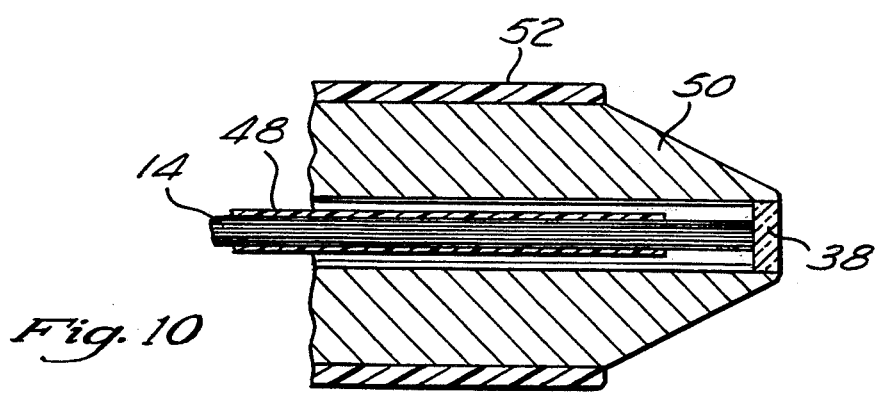

ENDOSCOPE WITH STERILE SLEEVE

FIELD OF THE INVENTION

The present invention relates generally to endoscopic devices and more particularly to an endoscope having a fiber optic image bundle insertible within a sterile sleeve such that the fiber optic image bundle need not be sterilized between uses.

BACKGROUND OF THE INVENTION

The use of endoscopes for diagnostic and therapeutic purposes is well known in the medical arts. Various types of endoscopes are available for various particular applications. For example, upper endoscopes are utilized for the examination of the esophagus, stomach, and duodenum; colonoscopes are utilized for the examination of the colon; angioscopes are utilized for the examination of various blood vessels; brochioscopes are utilized for examination of the bronchi; laparoscopes are utilized for examination of the peritoneal cavity; and arthroscopes are utilized for the examination of various joint spaces.

Although endoscopes provide tremendous advantage in the diagnosis and therapy of many medical conditions, contemporary endoscopes are limited in their capability for repeated use. In order to prevent the transmission of various pathogens, it is necessary to sterilize the endoscope between uses. This is of particular concern in contemporary times because of the threat of such vital infections as HIV and hepatitis B.

The sterilization of contemporary endoscopes presents several substantial disadvantages. First, the endoscope must be manufactured to withstand such sterilization. That is, the endoscope must be formed of materials which will not degrade in the presence of those sterilizing agents in contemporary use. This inherently requires that more expensive materials and manufacturing techniques be utilized and that the fiber optic image bundle be adequately isolated from or compatible with such sterilizing agents.

Second, thorough and proper sterilization of the endoscope requires particular care and is consequently a time-consuming operation. Of course, when the endoscope is being sterilized, it is not available for diagnostic and therapeutic use. Because of the high cost of endoscopes and the consequent lack of availability of spares, the down-time necessitated by sterilization represents lost income for the medical facility. This loss of income increases the cost of performing endoscopic procedures.

Third, even with the use of such effective sterilizing agents as glutaraldehyde, adequate sterilization of the endoscope cannot be assured. This is of particular concern when the endoscope has a working channel or other such difficult-to-clean portions. Furthermore, the use of such toxic materials as glutaraldehyde presents a hazard to the patient in that tissue irritations may result from inadequate flushing of the sterilizing agent from the endoscope. Additionally, special equipment such as a ventilated hood, is required in the use of such toxic sterilization agents, thus increasing the cost of performing such procedures.

For endoscopes having working channels, the currently accepted method of sterilization involves the use of a gas sterilization procedure wherein the endoscope is exposed to ethylene oxide gas sterilization protocol for a period of approximately twenty-four hours. As will be recognized, this involves an extended amount of time during which the endoscope is not available for diagnostic and therapeutic use. As with glutaraldehyde, ethylene oxide gas is extremely toxic. Therefore, exposure to personnel must be prevented and traces of the gas must be removed from the endoscope prior to its use to prevent tissue irritation.

It would also be beneficial to provide a disposable endoscope sleeve wherein the cost of the fiber optic bundle is eliminated from the cost of the sleeve, since only the sleeve need be purchased for each use. The fiber optic bundle is a one-time purchase. Thus, a new, sterile sleeve is purchased and used with the existing fiber optic bundle for each procedure.

SUMMARY OF THE INVENTION

The present invention specifically addresses and alleviates the above-mentioned deficiencies associated in the prior art. More particularly, the present invention comprises an endoscope having a fiber optic image bundle which is insertible into a separate sterile sleeve such that the fiber optic image bundle need not be sterilized prior to use. A window formed proximate the distal end of the sleeve facilitates viewing through the fiber optic image bundle. The sterile sleeve and the window cooperate to isolate the non-sterile fiber optic image bundle from the patient and thereby prevent the transmission of contagions from the fiber optic image bundle to the patient. A biasing or positioning means urges or positions the fiber optic image bundle into abutment with the window to insure proper optical alignment thereof.

The sleeve may be either disposable or reusable. Of course, if the sleeve is intended to be disposable, then it need not be manufactured to withstand repeated sterilization procedures. Disposable sleeves are simply replaced for each new procedure. Reusable sleeves are sterilized utilizing contemporary sterilization procedures. Sterilization of the sleeve only eliminates the problems associated with sterilization of the fiber optic image bundle. Furthermore, because the fiber optic image bundle is removed from the sleeve prior to sterilization, more diagnostic and therapeutic procedures can be performed and the cost of such procedures is reduced.

The biasing means preferably comprises an area of increased bore diameter proximate the proximal end of the sleeve wherein the fiber optic image bundle forms a bend such that it biases the distal end thereof into abutment with the window as it attempts to assume a straightened configuration. Thus, the length of the sleeve is formed to be shorter than the length of the image bundle to obtain biasing. This can alternately be accomplished without an area of increased bore diameter, preferably utilizing a stretchable sleeve. Those skilled in the art will recognize that various other biasing mechanisms are likewise suitable for assuring flush contact of the fiber optic image bundle with the window.

The window is attached to the sleeve via various means, i.e. ultrasonic welding, adhesive bonding, etc. The window may alternatively be formed at the distal end of the sleeve as an integral portion thereof. This is preferably accomplished by molding the window directly to the distal end of the sleeve wherein the distal end of the sleeve is placed into the window mold and a moldable transparent material is introduced into the mold, thus forming the window directly upon the sleeve. In any case, the window forms a leak-free seal to the sleeve such that pathogens disposed upon the unsterilized fiber optic image bundle do not come into contact with the patient.

The window is preferably formed of acrylic or polycarbonate and may optionally be formed to define a lens. The window is preferably formed at an angle of ninety degrees to the longitudinal axis of the sleeve to facilitate front viewing, but may optionally be formed at various other angles thereto to facilitate side viewing for particular applications. Those skilled in the art will recognize that various window angles are suitable for various diagnostic and therapeutic applications.

A working channel is optionally formed within the sleeve to facilitate the introduction of various utensils into the patient therethrough. Since the sleeve is sterilizable utilizing quick and effective sterilization procedures, the working channel formed therein does not prevent problems in the sterilization process.

The sleeve is preferably formed of a flexible material to facilitate use in intravascular applications and the like. However, the sleeve may optionally be formed of a rigid material suitable for use with trocars and the like. Alternatively, the window may optionally be formed directly upon the trocar and a fiber optic image bundle lacking a window inserted into the trocar.

An anti-reflective coating may optionally be applied to one or both sides of the window to improve light transmission therethrough and thereby enhance the quality of the image viewed through the fiber optic image bundle. Such anti-reflective coatings reduce the amount of light lost at the window due to reflections by approximately a factor of 2. Magnesium fluoride is an example of one such anti-reflective coating. Those skilled in the art will recognize that various other coating materials are likewise suitable. In addition to forming such an anti-reflective coating upon the window, the distal surface of the grin lens may similarly be treated. Coating both sides of the window and the distal side of the grin lens thus minimizes light lost due to reflections.

A reflective index matching oil or substance may optionally be disposed intermediate the grin lens and the window to minimize reflections occurring at these surfaces. Such oils or substances have an index of refraction which matches that of the grin lens and window as closely as possible. Preferably, a combination of such an index-matching oil or substance disposed intermediate the grin lens and window and the use of an anti-reflective coating on the exterior surface of the window provide optimum transmission of light to the image bundle.

These, as well as other advantages of the present invention, will be more apparent from the following description and drawings. It is understood that changes in the specific structure shown and described may be made within the scope of the claims without departing from the spirit of the invention.

BRIEF DESCRIPTION OF THE DRAWINGS

FIG. 1 is a perspective view of the endoscope of the present invention having the fiber optic image bundle inserted into the sleeve;

FIG. 2 is a perspective view of the endoscope of FIG. 1 having the fiber optic image bundle partially removed from the sleeve;

FIG. 3 is an enlarged view, partially in cross-section, of the proximal end of the fiber optic image bundle showing the biasing means;

FIG. 4A is a perspective view of the distal end of a first embodiment of the endoscope of the present invention with the window removed therefrom;

FIG. 4B is an enlarged perspective view of the distal end of the endoscope of FIG. 4A with the window installed thereon;

FIG. 4C is a perspective view of a second embodiment of the endoscope of the present invention;

FIG. 5 is an enlarged perspective view of the fiber optic image bundle showing the protective casing formed thereover;

FIG. 6 is a perspective view of an alternative configuration of the sleeve;

FIG. 7 is a cross-sectional side view taken along lines 7 of FIG. 6 showing abutment of the distal end of the fiber optic image bundle to the interior surface of the window;

FIG. 8 is an enlarged perspective view, partially in section, of the endoscope of FIG. 6;

FIG. 9 is a cross-sectional side view of the endoscope of the present invention being utilized with an embolectomy catheter and disposed within a blood vessel; and FIG. 10 is an enlarged cross-sectional view of an alternative configuration of the endoscope of the present invention for use within a trocar.

DETAILED DESCRIPTION OF THE PREFERRED EMBODIMENT

The detailed description set forth below in connection with the appended drawings is intended as a description of the presently preferred embodiments of the invention, and is not intended to represent the only forms in which the present invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The endoscope of the present invention is illustrated in FIGS. 1 through 10 which depict two presently preferred embodiments of the invention. Referring now to FIGS. 1 and 2, the first embodiment of the endoscope is generally comprised of a non-sterile portion 10 and a sterile portion 12. The non-sterile portion comprises a fiber optic image bundle 14 connected to an eyepiece 16 through which images communicated through the fiber optic image bundle 14 are viewed. As those skilled in the art will recognize, the image bundle preferably comprises fiber optics, but may alternatively comprise lenses, rods, mirrors, etc. Alternatively, a camera adapter may be utilized to facilitate attachment of the endoscope to a camera for recording and/or display of the images received thereby.

The fiber optic image bundle 14 extends from the eyepiece 16 through female bayonet connector 20 attached to the eyepiece 16 and through complimentary male bayonet connector 22 connected to sleeve 24. The male bayonet connector 22 and the sleeve 24 form a portion of the sterilized portion 12 of the endoscope of the present invention. Male bayonet connector 22 is formed upon body 28 to which sleeve 24 is attached. Body 28 is preferably formed of a molded material and facilitates handling of the sleeve 24. Illumination connector 26, likewise formed upon body 28, facilitates connection of an illumination source for the transmission of light through illumination fibers 44 (best shown in FIG. 4A) formed within the sleeve 24.

As those skilled in the art will recognize, the illumination fibers 44 may comprise fiber optic single fibers, fiber optic multiple fibers, hollow or solid light guides, rods, lenses, mirrors, etc. Optionally, the illumination fibers are formed along side of the fiber optic image bundle 14 and are insertible and removable from the sleeve 24 therewith.

A window 38 is formed upon and sealed to the distal end of sleeve 24, thereby closing the bore formed therethrough. The sleeve 24 and window 38 define a sleeve assembly.

A working channel 30 (best shown in FIGS. 4A and 4C) may optionally be formed along at least a portion of the length of the sleeve 24. Access to the channel 30 is provided via channel connection conduit 32 which attaches to sleeve 24 via Y 34. Connector 36 formed upon the distal end of channel connector facilitates the insertion of various tools and utensils into working channel 30. The working channel 30 additionally facilitates the introduction of transparent fluids therethrough for clearing the field of view.

Referring now to FIG. 3, a biasing means is formed, preferably as an integral part of eyepiece 16, to insure that the fiber optic image bundle 14 abuts window 38 formed at the distal end of sleeve 24. In the preferred embodiment of the present invention, the biasing means comprises a bore 40 having a diameter substantially greater than the diameter of the fiber optic image bundle 14 such that the fiber optic image bundle 14 forms bend 42 within bore 40. Bend 42 forms in the fiber optic image bundle 14 because the fiber optic image bundle 14 is slightly longer than the distance from the window to the eyepiece. Because of the attachment of the fiber optic image bundle 14 to the eyepiece 16, bend 42 urges the remainder of the fiber optic image bundle 14 distally, thus insuring abutment of the fiber optic image bundle 14 to the window 38. This biasing or positioning effect is achieved by forming the fiber optic image bundle 14 and sleeve 24 of different lengths, i.e. the fiber optic image bundle longer than the sleeve 24, such that when the fiber optic image bundle 14 is inserted into the sleeve 24 it is inherently forced against the window 38. Such abutment is necessary to insure proper imaging through window 38.

Optionally, the biasing means may be formed within or adjacent body 28 or elsewhere along the length of sleeve 24. Furthermore, those skilled in the art will recognize that various other, i.e. spring, pressurization, etc., means for assuring abutting contact of the fiber optic image bundle 14 with the window 38 are likewise suitable.

Referring now to FIGS. 4A and 4B, window 38 is attached to sleeve 24 in a manner which provides leak-free sealing thereof. Dimples 45 or other such non-smooth areas, i.e., ripples, lenses, roughen portions, frosted portions, etc., may optionally be formed in the window 38 proximate the illumination bundles 44 to effect dispersion of the light provided thereby, thus providing broader, less concentrated illumination. Window 38 is preferably permanently attached to the distal end of the sleeve 24. Those skilled in the art will recognize that various other means, i.e. adhesive bonding, ultrasonic welding, etc., are suitable. Alternatively, window 38 may be formed as an integral portion of sleeve 24 by positioning the distal end of sleeve 24 within a mold into which transparent material is injected to form window 38 directly upon the distal end of sleeve 24. The window 38 is preferably comprised of either an acrylic or polycarbonate material. It is essential that attachment of the window 38 to the sleeve 24 be leak free in order to assure that pathogens are not transferred from the non-sterile fiber optic image bundle 14 to the patient. Fiber optic illumination fibers 44 may either be formed as a part of sleeve 24 or may be insertible along with the fiber optic image bundle 14.

In those embodiments where the fiber optic illumination fibers 44 are insertible into the sleeve 24 along with the fiber optic image bundle 14, the fiber optic illumination fibers 44 are preferably formed or attached along fiber optic image bundle 14 such that an assembly of both the fiber optic image bundle 14 and the fiber optic illumination fibers 44 are insertible into the sleeve 24 as a unit.

Referring now to FIG. 4C, in a second embodiment of the present invention a window 46 is formed to cover only the fiber optic image bundle 14 such that working channel 30 is provided for various diagnostic and therapeutic procedures wherein various instruments and/or devices are passed therethrough. The working channel 30 is also used for the introduction of clear fluids which provide a transparent medium to facilitate viewing through the image bundle 14. For example, saline solution may be utilized to displace blood within the vascular system and thereby permit viewing of the vessel walls. Since they are not covered by window 46, fiber optic illumination fibers 44 preferably form a permanent part of sleeve 24 and thus are preferably not removable along with fiber optic image bundle 14.

Referring now to FIG. 5, a casing 48 is preferably formed about the fiber optic image bundle 14 to facilitate the handling thereof. Likewise, similar casings may be formed about the illumination fibers 44. The casings formed about the fiber optic image bundle 14 and/or the fiber optic illumination fibers 44 may optionally be flexible to facilitate uses in the vascular system and the like.

Referring now to FIG. 6, in those embodiments lacking the working channel, the requirement for a channel connection conduit is eliminated.

Referring now to FIG. 7, abutment of the fiber optic image bundle 14 to the window 38 is illustrated. The fiber optic image bundle 14 abuts in a flush manner to the window 38 such that the image transmitted therethrough is not distorted at the interface of the fiber optic image bundle 14 and the window 38.

As shown in FIG. 8, the fiber optic image bundle 14 is disposed within the casing 48 and inserted into sleeve 24 for use during diagnostic and therapeutic procedures.

Referring now to FIG. 10, the endoscope of the present invention is applicable to use with trocars and the like. The fiber optic image bundle 14, preferably encased within protective casing 48, is inserted into sleeve 50. Sleeve 50 is then inserted through trocar 52 to facilitate viewing. If required, fiber optic illumination fibers are inserted into trocar 52 along with, preferably as an integral unit, fiber optic image bundle 14. Those skilled in the art will recognize that various other such applications of the endoscope of the present invention are likewise suitable.

The endoscope can optionally be formed to have articulation or steering means, preferably formed within the sleeve, to facilitate insertion of the endoscope within blood vessels and the like.

Having defined the structure of the endoscope of the present invention, it may be beneficial to describe the operation thereof. With reference to FIG. 9, a procedure utilizing the endoscope of the present invention with a balloon or Fogerty (a registered trademark of Baxter Edwards of Irvine, Calif.) or embolectomy catheter is illustrated. The fiber optic image bundle 14 is inserted into sleeve 24 having a balloon 54 formed upon the distal end thereof proximate window 38. The distal end of the sleeve 24 is positioned as desired by viewing through window 38. In this instance, the distal end of sleeve 24 is positioned just past occlusion 56 formed in blood vessel 58. Balloon 54 is inflated and utilized to dislodge or break up occlusion 56.

At the conclusion of the procedure, the fiber optic image bundle 14 is removed from the sleeve 24. Sleeve 24 is then sterilized if it is to be used in a subsequent procedure or disposed of if it is of a disposable configuration. Fiber optic image bundle 14 need not be sterilized prior to subsequent use, but rather may be cleaned in a routine manner, i.e., washed with soap and water, if desired. Thus, fiber optic image bundle 14 is not exposed to chemicals, heat, etc. necessary for complete sterilization thereof. This is possible because of the barrier provided by sleeve 24 and window 38 formed upon the distal end thereof which facilitates the use of a non-sterile fiber optic image bundle 14.

It is understood that the exemplary endoscope described herein and shown in the drawings represents only presently preferred embodiments of the invention. Indeed, various modifications and additions may be made to such embodiments without departing from the spirit and scope of the invention. For example, those skilled in the art will recognize that various configurations of the window 38 are suitable. For example, side view windows, forty-five degree angle windows, etc., are well known in the art and suitable for use with the present invention. Additionally, various materials and/or configurations of the sleeve 24 are contemplated. The sleeve is preferably of a flexible material to facilitate use within blood vessels, but may optionally be of rigid construction for various applications. Thus, these and other modifications and additions may be obvious to those skilled in the art and may be implemented to adapt the present invention for use in a variety of different applications.

What is claimed is:

1. An endoscope comprising:
   a) a fiber optic image bundle;
   b) a sleeve having proximal and distal ends and having a bore formed therein, said bore having a diameter sized greater than said fiber optic image bundle such that said fiber optic image bundle is freely insertable through the proximal end into said bore;
   c) a window formed proximate the distal end of said sleeve;
   d) means for axially biasing the fiber optic image bundle toward said window such that said fiber optic image bundle is maintained in abutment with said window; and
   e) wherein said sleeve and said window isolate said fiber optic image bundle from a patient such that said fiber optic image bundle need not be sterilized prior to use.

2. An endoscope comprising:
   a) a fiber optic image bundle;
   b) a sleeve having proximal and distal ends and having a bore formed therein, said bore having a diameter sized greater than a fiber optic image bundle such that said fiber optic image bundle is freely insertable into the proximal end into said bore;
   c) a window formed proximate the distal end of said sleeve;
   d) Means for axially biasing the fiber optic image bundle towards said window such that said fiber optic image bundle is maintained in abutment with said window; and
   e) wherein said sleeve and said window are formed of a sterilizable material such that said sleeve is reusable.

3. An endoscope sleeve assembly comprising:
   a) a sleeve having proximal and distal ends and having a bore formed therein, said bore having a diameter sized greater than a fiber optic image bundle such that said fiber optic image bundle is freely insertable within said bore, said sleeve having a length shorter than said fiber optic image bundle;
   b) a window formed proximate the distal end of said sleeve; and
   c) wherein said length of said sleeve provides a biasing means for urging said fiber optic image bundle into abutment with said window when said fiber optic image bundle is disposed within said bore of said sleeve.

4. The endoscope sleeve assembly as recited in claim 3 wherein said sleeve has a bore configured such that at least one illumination fiber is also insertible therein.

5. The endoscope sleeve assembly as recited in claim 3 wherein said sleeve further comprises at least one illumination fiber.

6. The endoscope sleeve assembly as recited in claim 3 wherein said sleeve further comprises a working channel formed therein.

7. The endoscope sleeve assembly as recited in claim 3 wherein said sleeve is comprised of a flexible material.

8. The endoscope sleeve assembly as recited in claim 3 wherein said window is formed as an integral portion of said sleeve.

9. The endoscope sleeve assembly as recited in claim 3 wherein said sleeve, said window, and said biasing means are disposable.

10. An endoscope sleeve assembly comprising:
    a) a fiber optic image bundle;
    b) a sleeve having proximal and distal ends and having a bore formed therein, said bore having a diameter sized greater than said fiber optic image bundle such that said fiber optic image bundle is freely insertable within said bore, said sleeve having a length shorter than said fiber optic image bundle and being comprised of material suitable for repeated sterilization;
    c) a window formed proximate the distal end of said sleeve, said window being comprised of material suitable for repeated sterilization; and
    d) wherein said shorter length of said sleeve provides biasing means for urging and maintaining said fiber optic image bundle in abutment with said window when said fiber optic image bundle is inserted within said bore.

11. The endoscope sleeve assembly as recited in claim 10 wherein said sleeve has a bore configured such that at least one illumination fiber is also insertible therein.

12. The endoscope sleeve assembly as recited in claim 10 wherein said sleeve further comprises at least an illumination fiber.

13. The endoscope sleeve assembly as recited in claim 10 wherein said sleeve further comprises a working channel formed therein.

14. The endoscope sleeve assembly as recited in claim 10 wherein said sleeve is comprised of a flexible material.

15. The endoscope sleeve assembly as recited in claim 10 wherein said sleeve assembly further comprises means for axially biasing the fiber optic image bundle toward said window such that said fiber optic image bundle is maintained in abutment with said window, said means being comprised of materials suitable for repeated sterilization.

16. The endoscope sleeve assembly as recited in claim 10 wherein said window comprises a lens.

17. An endoscope comprising:
a) a fiber optic image bundle;
b) a sleeve having proximal and distal ends and having a bore formed therein such that said fiber optic image bundle is insertible through the proximal end into said bore;
c) a window formed proximate the distal end of said sleeve;
d) a biasing means formed about said fiber optic image bundle, said biasing means comprising a chamber having a diameter greater than the bore formed in said sleeve such that said image bundle forms a bend therein, the bend exerting a biasing force such that said image bundle is maintained in abutment with said window.

18. The endoscope as recited in claim 17 further comprising an anti-reflective coating formed upon at least one surface of said window.

19. The endoscope as recited in claim 18 further comprising a grin lens formed at the distal end of said fiber optic image bundle and having an anti-reflective coating formed upon the distal surface of said grin lens.

20. The endoscope as recited in claim 17 further comprising an index of refraction matching oil disposed intermediate said window and said grin lens.

21. The endoscope as recited in claim 17 further comprising:
a) an anti-reflective coating formed upon the distal end of said window; and
b) an index of refraction matching oil disposed intermediate said window and said grin lens.

22. A method for using an endoscope, the method comprising the steps of:
a) freely inserting a fiber optic image bundle into a bore of a sleeve, said sleeve having a window formed at the distal end thereof;
b) axially biasing the fiber optic image bundle toward said window such that the fiber optic image bundle is maintained in abutment with said window; and
c) wherein the fiber optic image bundle is isolated within the sleeve such that the fiber optic image bundle does not require sterilization.

23. The method as recited in claim 22 further comprising the step of inserting at least one illumination fiber into the sleeve.

24. The method as recited in claim 22 further comprising the step of utilizing a working channel formed within said sleeve.

25. The method as recited in claim 22 further comprising the steps of:
a) removing the fiber optic image bundle from the sleeve; and
b) disposing of the sleeve.

26. An endoscope sleeve assembly comprising:
a) a sleeve having proximal and distal ends and having a bore formed therein such that a fiber optic image bundle is insertable within said bore, said sleeve being comprised of materials suitable for repeated sterilization;
b) a window formed proximate the distal end of said sleeve, said window being comprised of materials suitable for repeated sterilization; and
c) a biasing means for urging a fiber optic image bundle disposed within said bore into abutment with said window, said biasing means being comprised of materials suitable for repeated sterilization.

27. An endoscope sleeve assembly comprising:
a) a sleeve having proximal and distal ends and having a bore formed therein such that a fiber optic image bundle is insertable within said bore;
b) a lens formed proximate the distal end of said sleeve; and
c) a biasing means for urging a fiber optic image bundle disposed within said bore into abutment with said lens.

28. A method for using an endoscope, the method comprising the steps of:
a) inserting a fiber optic image bundle into a sleeve having a window formed at the distal end thereof;
b) biasing the fiber optic image bundle into abutment with said window, the fiber optic image bundle being so isolated within the sleeve that, in use, the fiber optic image bundle does not require sterilization;
c) removing the fiber optic image bundle from the sleeve; and
d) sterilizing the sleeve.

* * * * *